United States Patent
Mochizuki

(10) Patent No.: US 8,770,705 B2
(45) Date of Patent: Jul. 8, 2014

(54) DROPLET DISCHARGE DETECTION DEVICE AND IMAGE FORMING APPARATUS INCLUDING DROPLET DISCHARGE DETECTION DEVICE

(75) Inventor: Takeshi Mochizuki, Ibaraki (JP)

(73) Assignee: Ricoh Company, Ltd., Tokyo (JP)

( * ) Notice: Subject to any disclaimer, the term of this patent is extended or adjusted under 35 U.S.C. 154(b) by 121 days.

(21) Appl. No.: 13/614,294

(22) Filed: Sep. 13, 2012

(65) Prior Publication Data

US 2013/0077099 A1    Mar. 28, 2013

(30) Foreign Application Priority Data

Sep. 26, 2011 (JP) ................... 2011-209489

(51) Int. Cl.
   B41J 29/393 (2006.01)
   B41J 2/045 (2006.01)

(52) U.S. Cl.
   CPC .................... B41J 2/0451 (2013.01)
   USPC .............................. 347/19; 347/23

(58) Field of Classification Search
   CPC ..... B41J 2/0451; B41J 2/2412; B41J 2/16579
   USPC ..................................... 347/19, 23
   See application file for complete search history.

(56) References Cited

U.S. PATENT DOCUMENTS

2009/0115812 A1    5/2009    Ito et al.
2009/0141057 A1    6/2009    Hayashi et al.

FOREIGN PATENT DOCUMENTS

| JP | 2007-118264 | 5/2007 |
|----|----|----|
| JP | 2008-012782 | 1/2008 |
| JP | 2009-113305 | 5/2009 |
| JP | 2009-132025 | 6/2009 |
| JP | 2011-031532 | 2/2011 |
| JP | 2011-037201 | 2/2011 |
| JP | 2011-083965 | 4/2011 |

OTHER PUBLICATIONS

F. Jenkins and H. White, "Fraunhofer Diffraction by a Single Opening," Fundamentals of Optics, Chapter 15, 2011, pp. 315-337.

Hiroshi Kawakita, "Fine Particle Visualization and Optical Scattering," Technical Research Laboratory, Shin Nippon Air Technologies Co., Ltd., Technical report, No. 12, pp. 77-80, 2006 (with English translation).

*Primary Examiner* — Julian Huffman

(74) *Attorney, Agent, or Firm* — Oblon, Spivak, McClelland, Maier & Neustadt, L.L.P.

(57) ABSTRACT

Disclosed is a droplet discharge detection device including a head array unit in which plural nozzles are arranged in a line; a light emitter configured to emit a light beam in a direction in which the nozzles are arranged, wherein the light emitter is disposed at a first end portion of the head array unit and the light emitter has an aperture for limiting a diameter of a light beam; and a light receiver configured to receive a scattered light beam of the light beam generated by a droplet, wherein the light receiver is disposed at a second end portion of the head array unit, the second end portion being opposite to the light emitter of the head array unit.

5 Claims, 13 Drawing Sheets

DROPLET DISCHARGE DETECTION DEVICE AND IMAGE FORMING APPARATUS INCLUDING DROPLET DISCHARGE DETECTION DEVICE

BACKGROUND OF THE INVENTION

1. Field of the Invention

Embodiments of the present invention relate to a droplet discharge detection device that detects a droplet discharging state of a head array unit and an image forming apparatus including the droplet discharge detection device.

2. Description of the Related Art

An inkjet recording apparatus has been known as an image forming apparatus such as a compound machine where a printer, a facsimile device, a copier, and a plotter are arbitrary combined. For example, the inkjet recording apparatus has been known as the image forming apparatus for which a droplet discharge recording method has been adopted. In the droplet discharge recording method, a recording head is utilized. The recording head discharges ink droplets. The image forming apparatus, for which the droplet discharge recording method has been adopted, discharges the ink droplets onto a sheet of paper being conveyed, and thereby forms an image (recording, typing, seal copying, and printing are used as synonyms).

In such an image forming apparatus (hereinafter, it will be referred to as the "inkjet recording apparatus"), the recording head performs recording by discharging the ink from nozzles onto the sheet of paper. Therefore, image quality degrades when a discharging failure occurs due to, for example, an increase of the ink viscosity caused by evaporation of a solvent from the nozzles, solidification of the ink, adhesion of dust, or mixing in bubbles.

A droplet discharge detection device has conventionally been known such that it detects a droplet discharging state of a recording head. For example, a droplet discharge detection device has been known where a direct light method has been adopted for detecting presence or absence of discharging of a droplet (cf. Patent Document 1 (Japanese Patent Laid-Open Application No. 2007-118264)). In the droplet discharge detection device, a light emitter is arranged at one side of a nozzle array of a recording device so as to emit laser light along a nozzle array, and a light receiver is arranged at the other side of the nozzle array so as to receive the light. Additionally, another droplet discharge detection device has been known where a forward-scattered light method has been adopted for detecting the presence or absence of the discharging of the droplet (cf. Patent Documents 2-6 (Japanese Patent Laid-Open Applications No.2008-12782, No. 2009-113305, No. 2009-132025, No. 2011-31532, and No. 2011-83965)). In the droplet discharge detection device, laser light is emitted from one side of a nozzle array of a recording head along the nozzle array. A light receiver is disposed at a position separated from an optical axis of the laser light at the other side of the nozzle array. The light receiver receives the light that has been scattered by the droplet.

When the droplet discharging state is detected by the forward-scattered light method, the light receiver is disposed at the position that is separated from the optical axis of the laser light so as to prevent the light receiver from receiving the direct light. That is, if the light receiver is disposed at a position close to the optical axis of the laser light, the light receiver may receive the direct light. A droplet discharge detection device has been known in which a light capture unit is disposed for preventing the laser light travelling straight without scattered by the droplet from straying to enter the light receiver disposed at the position separated from the optical axis (cf. Patent Document 2 (Japanese Patent Laid-Open Application No. 2008-12782) and Patent Document 3 (Japanese Patent Laid-Open Application No. 2009-113305)). Additionally, a method has been proposed where flare light of the laser light is prevented or adjusted by shielding (cf. Patent Document 4 (Japanese Patent Laid-Open Application No. 2009-132025), Patent Document 5 (Japanese Patent Laid-Open Application No. 2011-31532), and Patent Document 6 (Japanese Patent Laid-Open Application No. 2011-83965)).

As the flare light, light can be considered such that it has been internally reflected or scattered on a transmitting surface of a lens, at a periphery of a lens, or at a holder portion. However, since such light repeats reflections multiple times or travels along a random light path, the coherence is small. Therefore, such light gives only a small influence on an amount of scattered light, which depends on whether the droplet is discharged or not discharged.

On the other hand, the diffracted light from an aperture of a light emitter that travels in the direction toward the light receiver has higher coherence than that of the internally reflected light or the scattered light. The diffracted light from the aperture of the light emitter interferes with the scattered light from the droplet on the light receiver. Therefore, the diffracted light from the aperture of the light emitter has an effect to vary a light intensity depending on a variation of an optical path difference. The optical path difference may vary depending on an alignment error of the nozzles or on curved discharging. It is possible that the light scattered by the droplet vanishes due to such interference. The problem to be solved is to provide a droplet discharge detection device and an image forming apparatus including the droplet discharge detection device, with which discharging of a droplet can be detected while the light scattered by the droplet is prevented from vanishing due to the interference.

SUMMARY OF THE INVENTION

An objective of the embodiments of the present invention is to provide a droplet discharge detection device and an image forming apparatus including the droplet discharge detection device, with which discharging of a droplet can be detected while the light scattered by the droplet is prevented from vanishing.

In one aspect, there is provided a droplet discharge detection device including a head array unit in which plural nozzles are arranged in a line; a light emitter configured to emit a light beam in a direction in which the nozzles are arranged, wherein the light emitter is disposed at a first end portion of the head array unit and the light emitter has an aperture for limiting a diameter of a light beam; and a light receiver configured to receive a scattered light beam of the light beam generated by a droplet, wherein the light receiver is disposed at a second end portion of the head array unit, the second end portion being opposite to the light emitter of the head array unit, wherein, when a first direction in which the droplet is discharged from the nozzles is set to be an X direction, and when a second direction that is perpendicular to the X direction and that is perpendicular to the direction in which the nozzles are arranged is set to be a Y direction, a formula below is satisfied:

$$\int_{X_1}^{X_2}\int_{Y_1}^{Y_2}(Asc^2+2Adf\cdot Asc\cdot\cos[2\pi(L_{df}-L_{sc})/\lambda])dX_{PD}\,dY_{PD}>0,$$

wherein, in the formula, the $Y_{PD}$ is a Y-coordinate of a position in the Y direction on a light receiving surface of the light receiver, the $[Y_1, Y_2]$ is an effective detection range in the Y direction on the light receiving surface of the light receiver, the $X_{PD}$ is an X-coordinate of the position in the X direction on the light receiving surface of the light receiver, the $[X_1, X_2]$ is an effective detection range in the X direction on the light receiving surface of the light receiver, the $L_{df}$ is a first optical path length of a diffracted light beam from a center of the aperture of the light emitter to the light receiving surface of the light receiver, the $A_{df}$ is a first amplitude of the diffracted light beam, the $A_{sc}$ is a second amplitude of the scattered light beam, the $L_{sc}$ is a second optical path length of the scattered light beam from the center of the aperture of the light emitter to the light receiving surface of the light receiver, and the $\lambda$ is the wavelength of the light beam.

With such a configuration, it is possible to provide the droplet discharge detection device and the image forming apparatus including the droplet discharge detection device, with which discharging of the droplet can be detected while the light scattered by the droplet is prevented from vanishing.

Other objects, features and advantages of the present invention will become more apparent from the following detailed description when read in conjunction with the accompanying drawings.

DETAILED DESCRIPTION OF THE PREFERRED EMBODIMENTS

Hereinafter, embodiments of the present invention will be explained while referring to the accompanying figures.

First Embodiment

Figure 1:
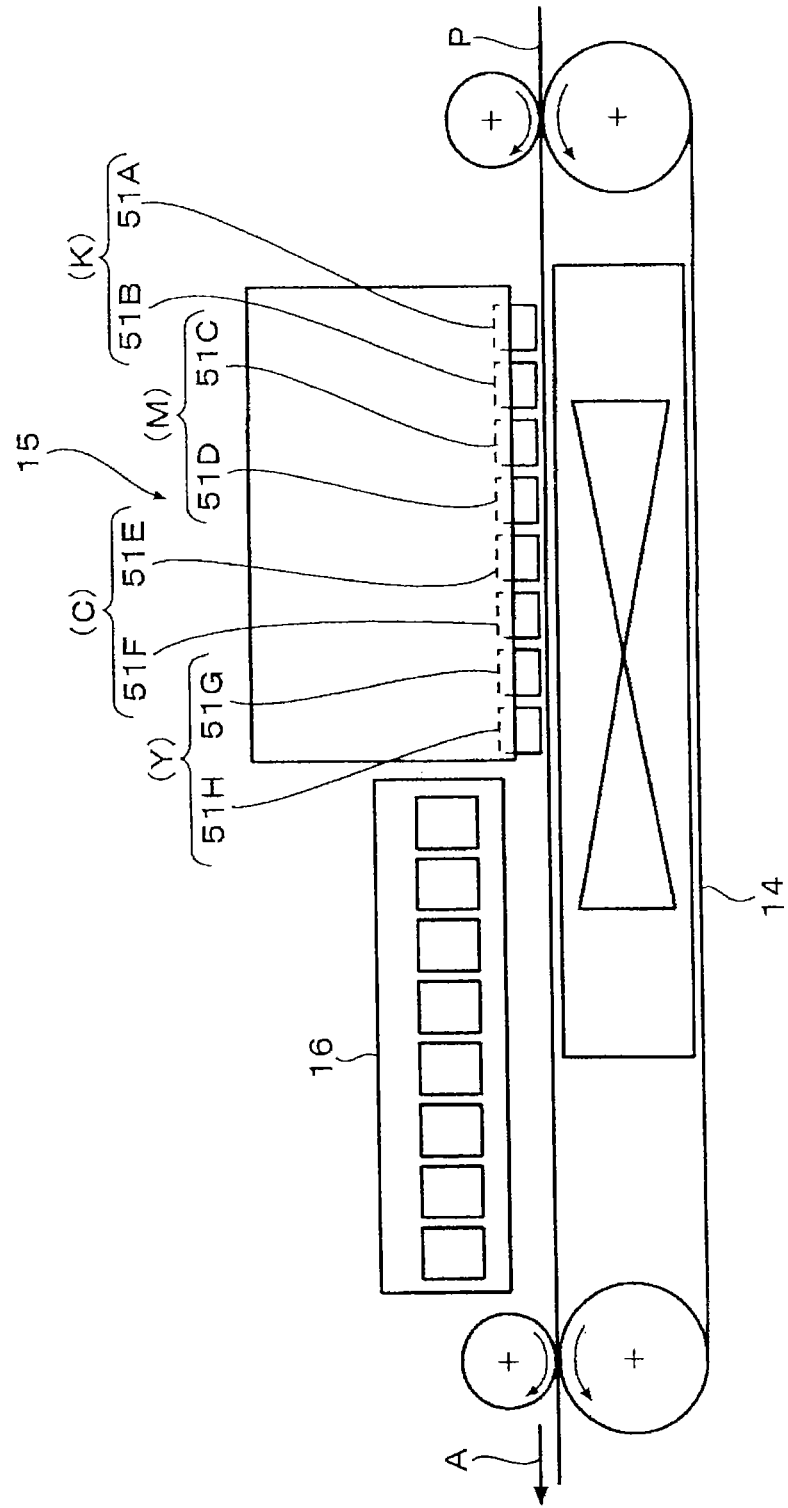
FIG. 1 is a schematic configuration diagram of an image forming apparatus according to a first embodiment.

FIG. 1 is a schematic configuration diagram of an image forming apparatus according to a first embodiment. As shown in FIG. 1, the image forming apparatus includes a conveyance unit 14 that conveys a sheet of paper P; a recording head unit 15 that discharges ink droplets toward the sheet of paper P, which has been conveyed by the conveyance unit 14, and thereby performing printing; and a head maintenance unit 16 that is a maintenance and recovering mechanism for the recording head unit 15.

The head maintenance unit 16 is disposed so that it can be slid above the conveyance unit 14 in a direction A in which the sheet of paper P is conveyed. When the head maintenance is performed, the head maintenance unit 16 moves below the recording head unit 15 after the recording head unit 15 has been moved upward. The head maintenance unit 16 is retracted to the position shown in FIG. 1, except at the time of performing the head maintenance.

Figure 2:
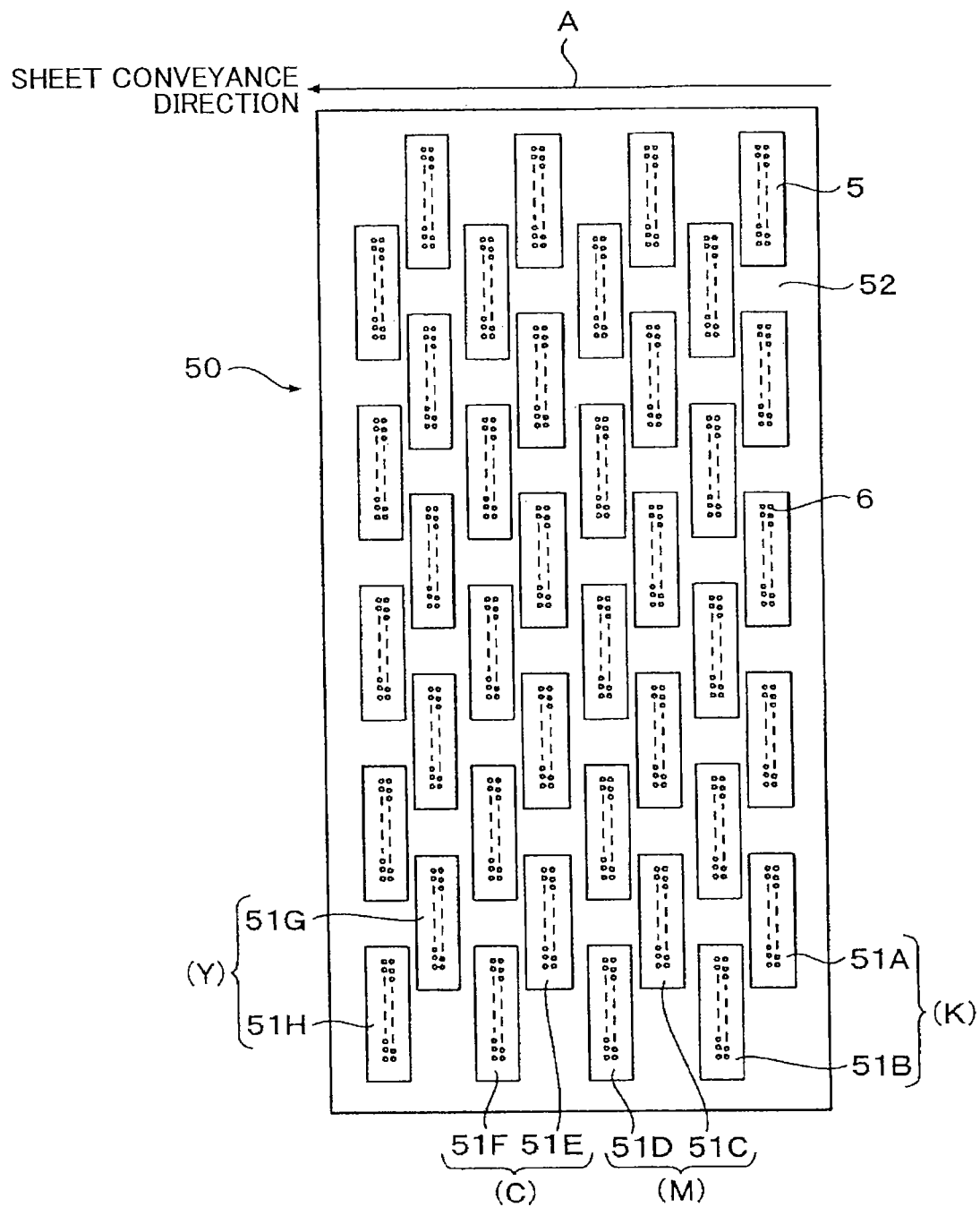
FIG. 2 is a magnified bottom view of a recording head unit that is utilized in the image forming apparatus.

FIG. 2 is a magnified bottom view of the recording head unit 15. As shown in FIG. 2, the recording head unit 15 includes a head array unit 50 including eight head sequences 51A-51H. Each of the head sequences 51A-51H includes plural heads 5 (in the first embodiments, five heads) arranged in a line on a base substrate 52. At the bottom surface of each of the heads 5, multiple nozzles 6 are arranged in two lines. The head sequences 51A-51H and the nozzle arrays 6 are arranged in a direction that is perpendicular to the direction A in which the sheet of paper P is conveyed.

Two nozzle arrays of the heads 5 included in the head sequences 51A and 51B discharge black (K) droplets. Two nozzle arrays of the heads 5 included in the head sequences 51C and 51D discharge magenta (M) droplets. Two nozzle arrays of the heads 5 included in the head sequences 51E and 51F discharge cyan (C) droplets. Two nozzle arrays of the heads 5 included in the head sequences 51G and 51H discharge yellow (Y) droplets.

Namely, one nozzle array corresponding to a width of the sheet of paper is formed by four nozzle arrays of the heads 5, that is, one nozzle array corresponding to the width of the sheet of paper is formed by two head sequences 51. The neighboring head sequences are arranged in a staggered manner, where the positions of the head sequences are shifted with each other in the direction in which the nozzles are arranged, so that the head sequences are staggered with each other. The arrangement of the lines of the corresponding colors is not limited to the above-described example. The arrangement of the colors is not limited to a particular arrangement. Further, the configuration of the recording head unit 15 is not limited to the above-described example.

The droplet discharge detection device has an arrangement (configuration) such that a diffracted light beam emitted from an aperture (in the first embodiment, a center opening portion of an aperture 4, described later) of a light emitter (hereinafter, it is merely referred to as the diffracted light) and a scattered light from a droplet (hereinafter, it is merely referred to as the scattered light) satisfy a condition that an interference term between the diffracted light beam and the scattered light beam becomes smaller than a light intensity of the scattered light within an effective range of a light receiver having a certain area.

Figure 3:
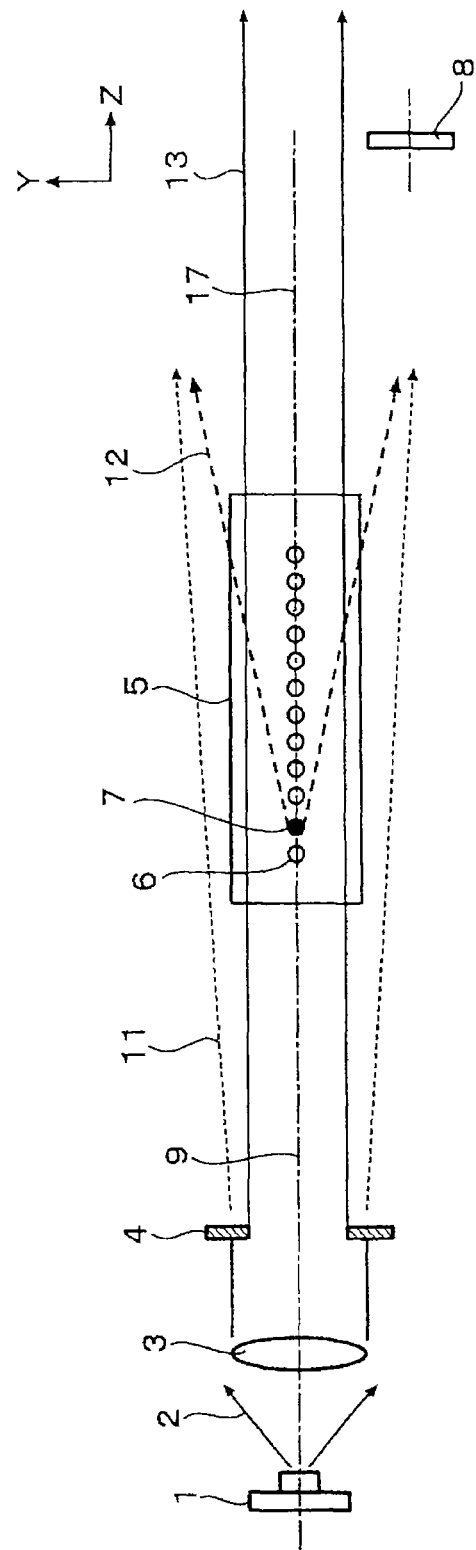
FIG. 3 is a schematic diagram where a droplet discharge detection device according to the first embodiment is viewed from a top surface.
Figure 4:
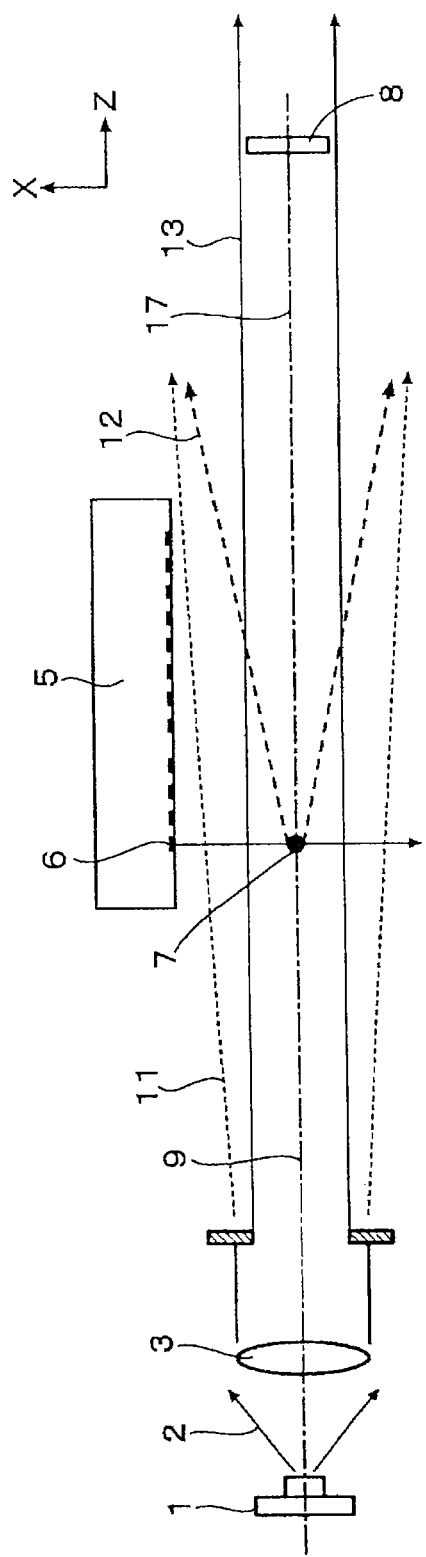
FIG. 4 is a schematic diagram where the droplet discharge detection device is viewed from a side surface.

The specific configuration will be explained while referring FIGS. 3 and 4. FIG. 3 is a schematic diagram of the droplet discharge detection device, where the droplet discharge detection device is viewed from a top surface. FIG. 4 is a schematic diagram of the droplet discharge detection device, where the droplet discharge detection device is viewed from a side surface. In FIGS. 3 and 4, the reference numeral 1 indicates a laser diode (LD) that functions as a light emitter; the reference numeral 2 indicates a laser beam that is emitted from the LD 1; the reference numeral 3 indicates a collimator lens that collimates the laser beam 2; the reference numeral 4 indicates an aperture that limits a diameter of the collimated laser beam 2; the reference numeral 5 indicates a head that discharges droplets; the reference numeral 6 indicates a nozzle disposed in the head 5, which is a discharging port for discharging droplets; the reference numeral 7 indicates a droplet discharged from the nozzle 6; the reference numeral 8 indicates a photodiode (PD) that is a light receiver; the reference numeral 9 indicates an optical axis of the laser beam 2; the reference numeral 11 indicates a diffracted light beam from the aperture 4; and the reference numeral 12 indicates a scattered light beam.

As shown in FIG. 3, multiple nozzles 6 are arranged along a line on the head 5. The projection of the line, along which the multiple nozzles 6 are arranged, onto the YZ plane is indicated by the reference numeral 17. However, in FIG. 3, the optical axis 9 of the laser beam and the line 17, along which the nozzles 6 are arranged, are on the same line.

The laser beam 2 emitted from the LD 1 travels in a direction in which the nozzles 6 are arranged (hereinafter, it is referred to as the Z direction). Therefore, the optical axis of the laser beam is in parallel with the Z direction. The PD 8 has a finite length in a direction in which the droplet is discharged (hereinafter, it is referred to as the X direction), and the PD 8 has a finite length in a direction perpendicular to the X direction and the Z direction (hereinafter, it is referred to as the Y direction). The PD 8 has an effective surface in the X-Y plane.

Further, as shown in FIG. 3, the PD 8 is not disposed on an extended line of the optical axis 9 of the laser beam 2. The PD 8 is disposed at a position which is shifted from the extended line of the optical axis 9 in the Y direction, so as to prevent the laser beam 2, whose diameter has been limited by the aperture 4, from entering the PD 8.

The diffracted light beam 11 and the scattered light beam 12 are portions of the leaser beam 2. In this description, the laser beam 2 that does not include the diffracted light beam 11 and the scattered light beam 12 is referred to as a direct light beam 13. Therefore, as shown in FIG. 3, the PD 8 is arranged so that the direct light beam 13 does not enter the PD 8.

Figure 5:
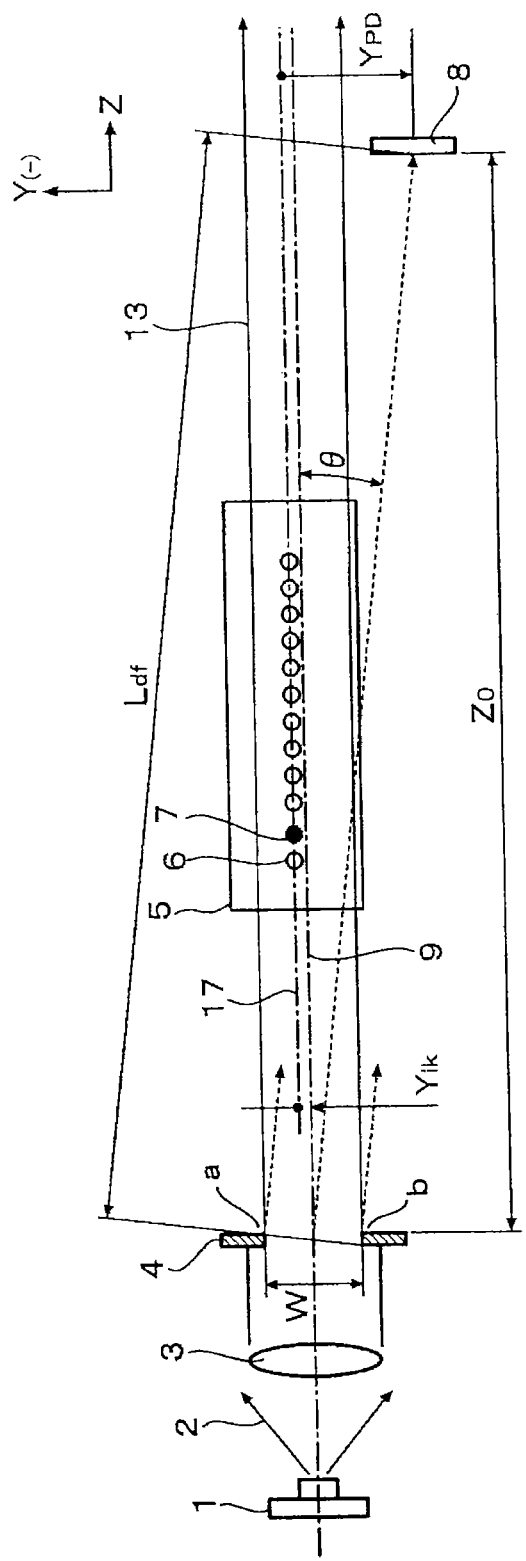
FIG. 5 is a diagram illustrating an optical path length of a diffracted light beam in the droplet discharge detection device, where the droplet discharge detection device is viewed from the top surface.
Figure 6:
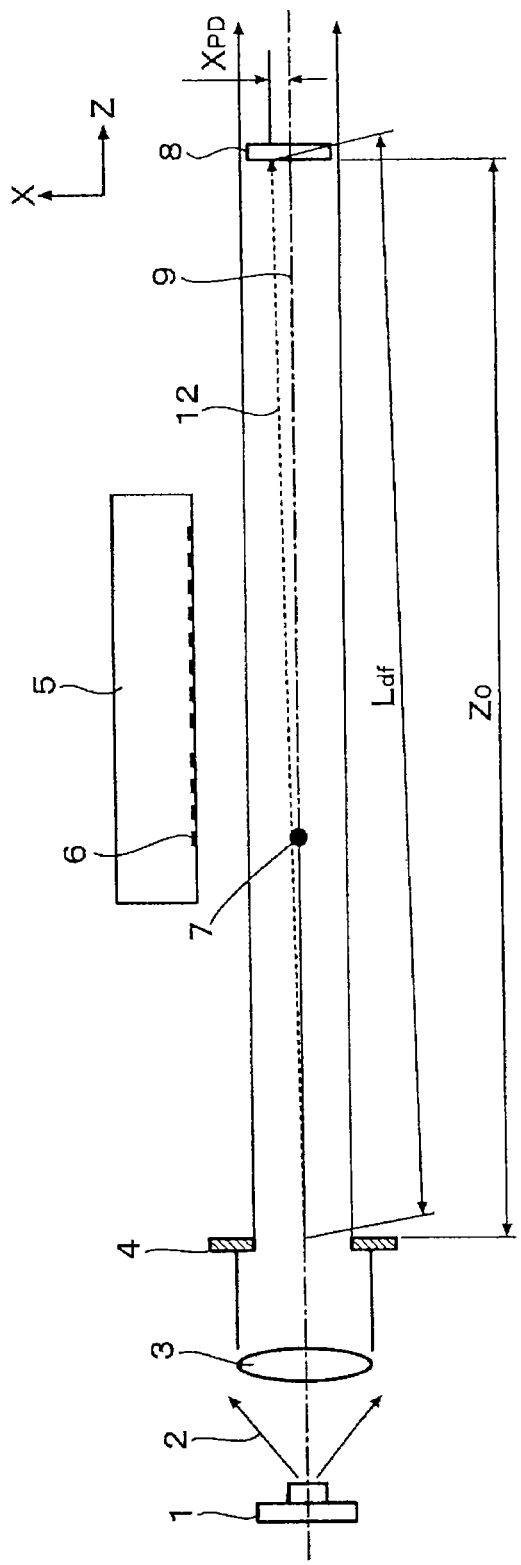
FIG. 6 is a diagram illustrating the optical path length of the diffracted light beam in the droplet discharge detection device, where the droplet discharge detection device is viewed from the side surface.

Hereinafter, there will be explained an optical path length of the diffracted light beam 11 by referring to FIGS. 5 and 6. FIG. 5 is a schematic diagram illustrating the droplet discharge detection device, where the droplet discharge detection device is viewed from the top surface. FIG. 6 is a schematic diagram illustrating the droplet discharge detection device, where the droplet discharge detection device is viewed from the side surface. As shown in FIG. 5, a distance between the line 17, along which the nozzles 6 are arranged, and the optical axis 9 of the laser beam 2 is $Y_{ik}$. The diffracted light beam 11 has an intensity distribution of light and shade on an observation plane including the PD 8 (cf. Non-Patent Document 1 (Fundamentals of Optics, chapter 15, F. Jenkins, H. White)). Consider a light beam that is diffracted in a direction of angle θ from the aperture 4 (cf. FIG. 5). Since the zero-th order diffracted light is the direct light beam 13, here, the diffracted light beam 11 means a diffracted light beam having an order that is greater than or equal to the plus first order or an order that is less than or equal to the minus first order.

When the diameter of the aperture 4 is W, the wavelength of the laser beam 2 is λ, and n is an integer greater than or equal to 1, if the formula (1) below is satisfied, a dark band is observed. That is because the light beams within the aperture 4 cancel out each other due to the phase difference of λ/2.

$$W \sin \theta = n\lambda \tag{1}$$

On the other hand, if the formula (2) below is satisfied, remaining light beams take a maximum value. Thus a light band is observed. Here, the remaining light beams are light beams that remain when the light beams that cancel out each other due to the phase difference of λ/2 are removed from the light beams within the aperture 4.

$$W \sin \theta = (2n+1)(\lambda/2) \tag{2}$$

The diffracted light beam 11 is not limited within a specific range in the Y direction, but the diffracted light beam 11 is distributed within a range of 0<sin θ<1, while alternately taking dark bands and light bands.

As shown in FIG. 6, an optical path length $L_{df}$ of the diffracted light beam 11 can be expressed by the formula (3) below by using the light passing through the center of the aperture 4.

$$L_{df} = \mathrm{SQRT}[Z_0^2 + (Y_{PD} - Y_{ik})^2 + X_{PD}^2] \tag{3}$$

In the formula (3), $L_{df}$ is the optical path length of the diffracted light beam 11 from the center of the aperture 4 to the light receiving surface of the PD 8 (cf. FIG. 6), $Z_0$ is the distance between aperture 4 and the light receiving surface of the PD 8 in the Z direction (cf. FIGS. 5 and 6), $Y_{PD}$ is a Y-coordinate of an arbitrary position on the PD 8 while setting the line 17 as a reference (cf. FIG. 5), and $X_{PD}$ is an X-coordinate of the arbitrary position on the PD 8 while setting the line 9 as the reference (cf. FIG. 6).

Figure 7:
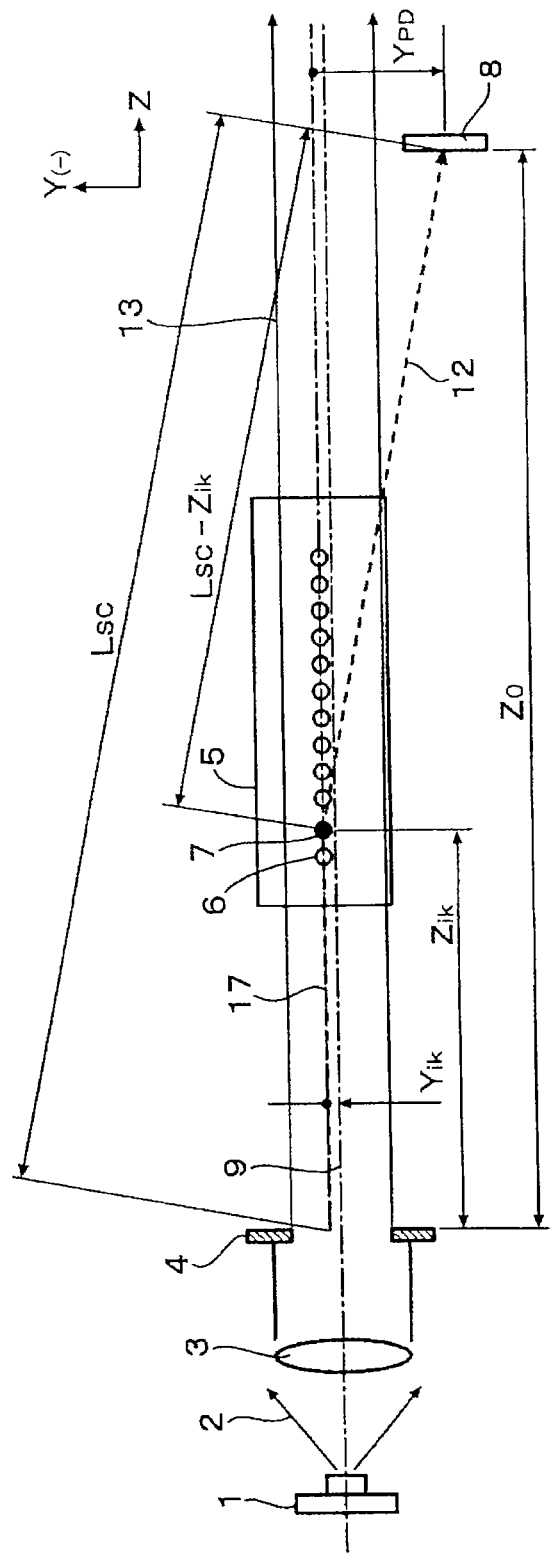
FIG. 7 is a diagram illustrating an optical path length of a scattered light beam in the droplet discharge detection device, where the droplet discharge detection device is viewed from the top surface.
Figure 8:
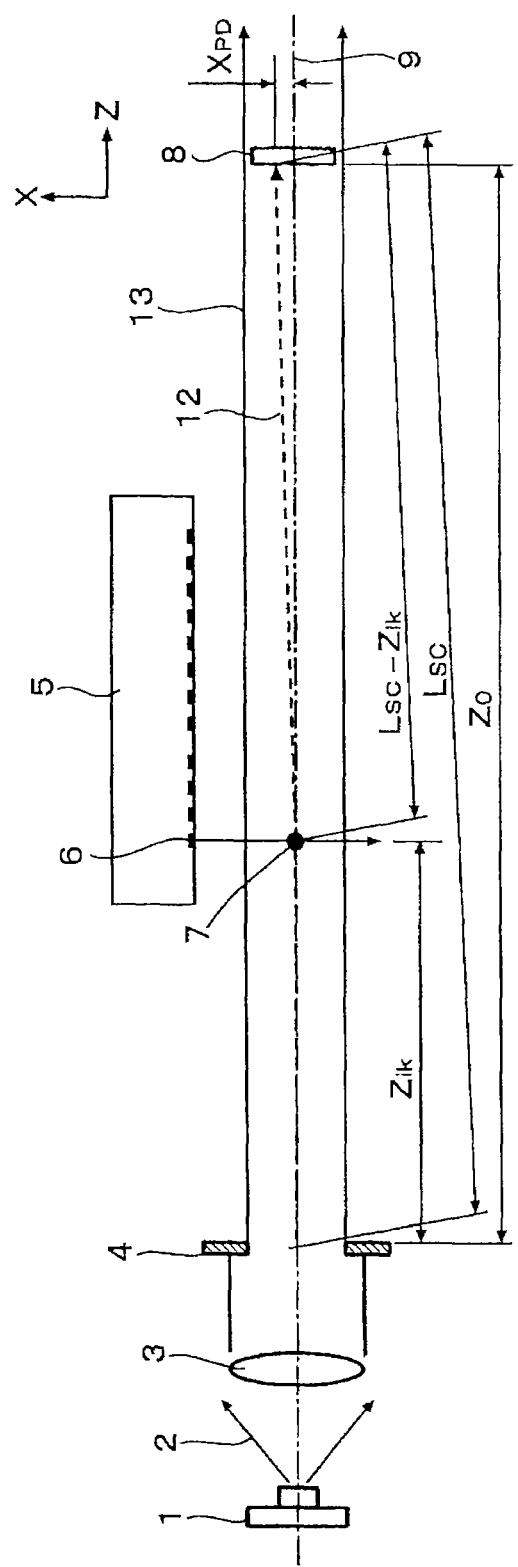
FIG. 8 is a diagram illustrating the optical path length of the scattered light beam in the droplet discharge detection device, where the droplet discharge detection device is viewed from the side surface.

Next, there will be explained an optical path length of the scattered light beam 12, while referring to FIGS. 7 and 8. FIG. 7 is a schematic diagram illustrating the droplet discharge detection device, where the droplet discharge detection device is viewed from the top surface. FIG. 8 is a schematic diagram illustrating the droplet discharge detection device, where the droplet discharge detection device is viewed from the side surface. Scattering angles of the scattered light beams 12 are distributed in accordance with a scattering angle distribution that depends on the diameter of the droplet and the wavelength of the laser (cf. Non-Patent Document 2 (Hiroshi Kawakita, "Fine Particle Visualization and Optical Scattering," Technical Research Laboratory, Shin Nippon Air Technologies Co., Ltd., Technical report, No. 12, pp. 77-80, 2006)). Among components of the scatted light beam 12, the components that are included in a solid angle spanned by the effective surface of the PD 8 enter the PD 8. The laser beams that enter the droplet 7 include the above-described diffracted light beams 11 having the orders greater than or equal to the plus first order and having the orders less than or equal to the minus first order. However, since these diffracted light beams 11 have lower light intensities relative to that of the direct light beam 13, only the direct light beam 13 will be considered.

From the opening portion of the aperture 4 to the position of the droplet 7, the direct light beam 13 travels a light path that is parallel to the optical axis 9 of the laser beam 2. From the droplet 7 to the PD 8, the scattered light beam 12 travels a light path that is inclined with respect to the optical axis 9 of the laser beam 2 by a certain angle. The optical path length $L_{sc}$ of the scattered light beam 12 is expressed by the formula (4) below.

$$L_{sc}=Z_{ik}+\mathrm{SQRT}[(Z_0-Z_{ik})^2+Y_{PD}^2+X_{PD}^2] \qquad (4)$$

In the formula (4), $L_{sc}$ is an optical path length of the scattered light beam 12 from the aperture 4 to the light receiving surface of the PD 8 (cf. FIGS. 7 and 8), $Z_{ik}$ is an optical path length from the aperture 4 to the position of the droplet 7 (cf. FIGS. 7 and 8), $Z_0$ is a distance from the aperture 4 to the light receiving surface of the PD 8 (cf. FIGS. 7 and 8), $Y_{PD}$ is a Y-coordinate of an arbitrary position on the PD 8 while setting the line 17 as a reference (cf. FIG. 7), and $X_{PD}$ is an X-coordinate of the arbitrary position on the PD 8 while setting the line 9 as the reference (cf. FIG. 8).

The oscillation of the diffracted light beam 11 at the arbitrary position $(X_{PD}, Y_{PD})$ on the PD 8 is expressed by the formula (5) below. Similarly, the oscillation of the scattered light beam 12 at the arbitrary position $(X_{PD}, Y_{PD})$ on the PD 8 is expressed by the formula (6) below.

$$Pdf=Adf \cdot \sin(2\pi ct/\lambda - \alpha df) \qquad (5)$$

$$Psc=Asc \cdot \sin(2\pi ct/\lambda - \alpha sc) \qquad (6)$$

In the formulae (5) and (6), Pdf is the oscillation of the diffracted light beam 11, Psc is the oscillation of the scattered light beam 12, Adf is the amplitude of the diffracted light beam 11, Asc is the amplitude of the scattered light beam 12, c is the speed of light, $\alpha df$ is the phase of the diffracted light beam 11, and $\alpha sc$ is the phase of the scattered light beam 12.

When both the diffracted light beam 11 and the scattered light beam 12 exist, namely, when the droplet 7 is discharged, the light intensity at the arbitrary position $(X_{PD}, Y_{PD})$ on the PD 8 is expressed by the formula (7) below.

$$Idfsc=Pdf^2+Psc^2=Adf^2+Asc^2+2Adf \cdot Asc \cdot \cos(\alpha df-\alpha sc) \qquad (7)$$

In the formula (7), Idfsc is the light intensity at the arbitrary position $(X_{PD}, Y_{PD})$ on the PD 8 during discharging of the droplet 7, Pdf is the oscillation of the diffracted light beam 11, Psc is the oscillation of the scattered light beam 12, Adf is the amplitude of the diffracted light beam 11, Asc is the amplitude of the scattered light beam 12, $\alpha df$ is the phase of the diffracted light beam 11, and $\alpha sc$ is the phase of the scattered light beam 12.

The first and second terms are simple summations of the light intensities, respectively. The third term is the interference term.

In a case where only the diffracted light beam 11 exists, namely, when the droplet 7 is not discharged, the light intensity at the arbitrary position $(X_{PD}, Y_{PD})$ on the PD 8 is expressed by the formula (8) below by setting Acs=0 in the formula (7).

$$Idf=Adf^2 \qquad (8)$$

The difference in the light intensity caused by the droplet 7 being discharged is expressed by the formula (9) by evaluating the difference between the formula (7) and the formula (8).

$$Idfsc-Idf=Asc^2+2Adf \cdot Asc \cdot \cos(\alpha df-\alpha sc) \qquad (9)$$

Here, the difference between the phases can be expressed by the formula (10) below, based on the optical path difference.

$$\alpha df-\alpha sc=2\pi(L_{df}-L_{sc})/\lambda \qquad (10)$$

By substituting the formula (10) in the formula (9), the formula (11) below is obtained.

$$Idfsc-Idf=Asc^2+2Adf \cdot Asc \cdot \cos[2\pi(L_{df}-L_{sc})/\lambda] \qquad (11)$$

When the effective detection range in the X direction on the light receiving surface of the PD 8 is from $X_1$ to $X_2$, and the effective detection range in the Y direction on the light receiving surface of the PD 8 is from $Y_1$ to $Y_2$, the amount of light V entering the PD 8 is expressed by the formula (12) below, where (Idfsc−Idf) is double integrated within the effective detection range with respect to $(X_{PD}, Y_{PD})$.

$$V=\int_{X_1}^{X_2}\int_{Y_1}^{Y_2}(Idfsc-Idf)dX_{PD}dY_{PD}=\int_{X_1}^{X_2}\int_{Y_1}^{Y_2}(Asc^2+2+ Adf \cdot Asc \cdot \cos[2\pi(L_{df}-L_{sc})/\lambda])dX_{PD}dY_{PD} \qquad (12)$$

In the formula (12), V is the amount of light entering the PD 8, $Y_{PD}$ is the Y-coordinate of the arbitrary position on the PD 8 when the line 17 is set to be the reference, $[Y_1, Y_2]$ is the effective detection range in the Y direction on the light receiving surface of the PD 8, $X_{PD}$ is the X-coordinate of the arbitrary position on the PD 8 when the line 9 is set to be the reference, $[X_1, X_2]$ is the effective detection range in the X direction on the light receiving surface of the PD 8, Idfsc is the light intensity at the arbitrary position $(X_{PD}, Y_{PD})$ on the PD 8 during discharging of the droplet 7, Idf is the light intensity at the arbitrary position $(X_{PD}, Y_{PD})$ on the PD 8 when the droplet 7 is not discharged, Asc is the amplitude of the scattered light beam 12, Adf is the amplitude of the diffracted light beam 11, $L_{df}$ is the optical path length of the diffracted light beam 11 from the center of the aperture 4 to the light receiving surface of the PD 8, $L_{sc}$ is the optical path length of the scattered light 12 from the aperture 4 to the PD 8, and $\lambda$ is the wavelength of the laser beam 2.

A condition that the scattered light beam 12 can be detected is that the integrated value of the amount of the light on the PD 8 when the scattered light beam 12 is superposed on the diffracted light beam 11 is increased relative to the integrated value of the amount of the light on the PD 8 when only the diffracted light beam 11 exists. Therefore, the condition that the amount of the light V entering the PD 8 satisfies the inequality V>0 is a condition where droplet detection is possible.

The amount of the light V is varied depending on the Y-directional distance $Y_{ik}$ between the arrangement line 17 of the nozzles 6 and the optical axis 9 of the laser beam 2. Since $L_{sc}$ expressed by the formula (4) does not include $Y_{ik}$ and $L_{df}$ expressed by the formula (3) includes $Y_{ik}$, the phase of the interference term (Idfsc−Idf) is varied by varying $Y_{ik}$.

As a specific method of varying $Y_{ik}$, a configuration can be adopted such that the light emitter that integrates the LD 1, the collimator lens 3, and the aperture 4 having the opening portion can be moved in the Y direction.

Figure 9:
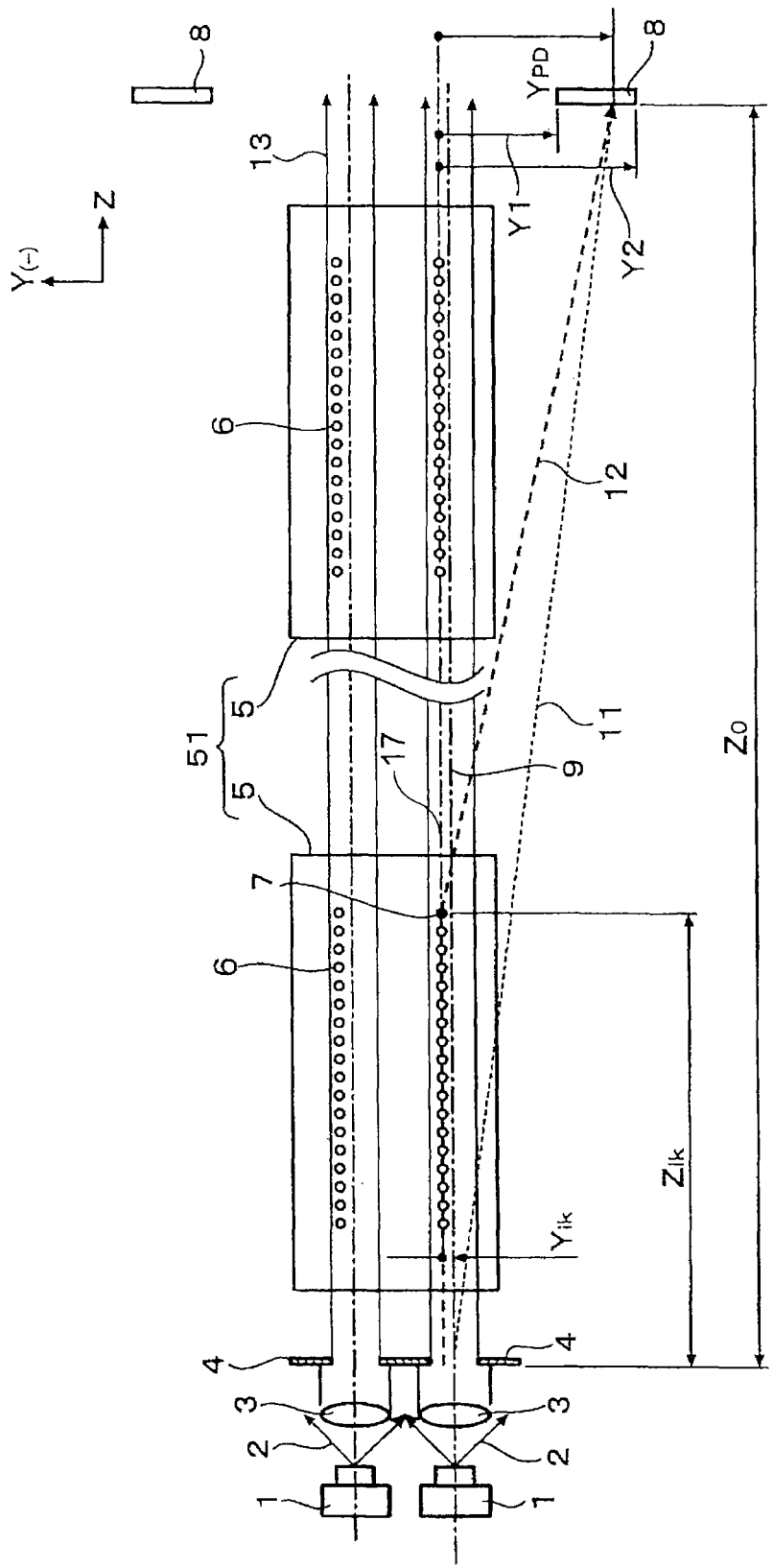
FIG. 9 is a schematic diagram illustrating a head array unit including the droplet discharge detection device according to the first embodiment.

FIG. 9 is a schematic diagram illustrating a head array unit including the droplet discharge detection unit according to the first embodiment. A part of the head sequence 51 is shown in FIG. 9.

In FIG. 9, the reference numerals 1 indicate laser diodes (LD) that function as light emitters; the reference numerals 2 indicate laser beams that are emitted from the corresponding LDs 1; the reference numerals 3 indicate collimator lenses that collimate the corresponding laser beams 2; the reference numerals 4 indicate apertures, each having an opening for limiting a diameter of the corresponding collimated laser beam 2; the reference numerals 5 indicate heads that discharge corresponding droplets 7; the reference numerals 6 indicate nozzles, which are discharging ports for discharging the corresponding droplets 7; the reference numerals 8 indicate photodiodes (PD) that are light receivers; the reference numeral 9 indicates an optical axis of one of the leaser beams 2; the reference numeral 11 indicates a diffracted light beam from one of the apertures 4; and the reference numeral 12 indicates a scattered light beam.

As shown in FIG. 9, plural nozzles 6 are arranged in lines in the heads 5. A projection of one of the lines, along which the corresponding nozzles 6 are arranged, onto the Y-Z plane is indicated the reference numeral 17. The laser beam 2 emitted from one of the LDs 1 travels in the Z direction, and the optical axis 9 of the laser beam 2 is in parallel with the Z-direction.

Each of the PDs 8 has a finite length in the X direction and a finite length in the Y direction. Further, the PD 8 is not disposed on the extended line of the optical axis 9 of the laser beam 2. The PD 8 is disposed at a position shifted from the optical axis 9 in the Y direction, so as to prevent the laser beam 2 from entering the PD 8.

As shown in FIG. 9, the droplet discharge detection devices, each formed of the LD 1, the collimator lens 3, the aperture 4, and the PD 8, are provided for each of the nozzle arrays 51. The light emitter formed of the LD 1, the collimator lens 3, and the aperture 4 is disposed at a side of one end portion of the nozzle array 51. The light receiver formed of the PD 8 is disposed at a side of the other end portion of the nozzle array 51, which is opposite to the side of the light emitter.

In FIG. 9, $Z_0$ indicates the distance between the aperture 4 and the PD 8 in the Z direction, $Y_{PD}$ is the Y-coordinate of an arbitrary position on the PD 8 when the line 17 is set to be the reference, $X_{PD}$ (cf. FIG. 8) is the X-coordinate of the arbitrary position on the PD 8 when the optical axis 9 of the laser beam 2 is set to be the reference, $Y_{ik}$ is the Y-directional distance between the arrangement line 17 of the nozzles 6 and the optical axis 9 of the laser beam 2, and $Z_{ik}$ is the Z-directional distance between the aperture 4 and the droplet. Further, $\lambda$ is the wavelength of the laser beam 2.

In the first embodiment, the following numerical values have been adopted for designing the droplet discharge detection device.

$Z_0$=731 mm
X=650 nm
$X_1$=−0.01875 mm
$X_2$=+0.01875 mm
$Y_1$=3.1125 mm
$Y_2$=6.4875 mm
$Asc^2$=1×10$^{-6}$ W/mm$^2$
$Adf^2$=5×10$^{-7}$ W/mm$^2$, 1×10$^{-6}$ W/mm$^2$, 1.5×10$^{-6}$ W/mm$^2$
$Z_{ik}$=74 mm, 355 mm, 635 mm

Figure 10:
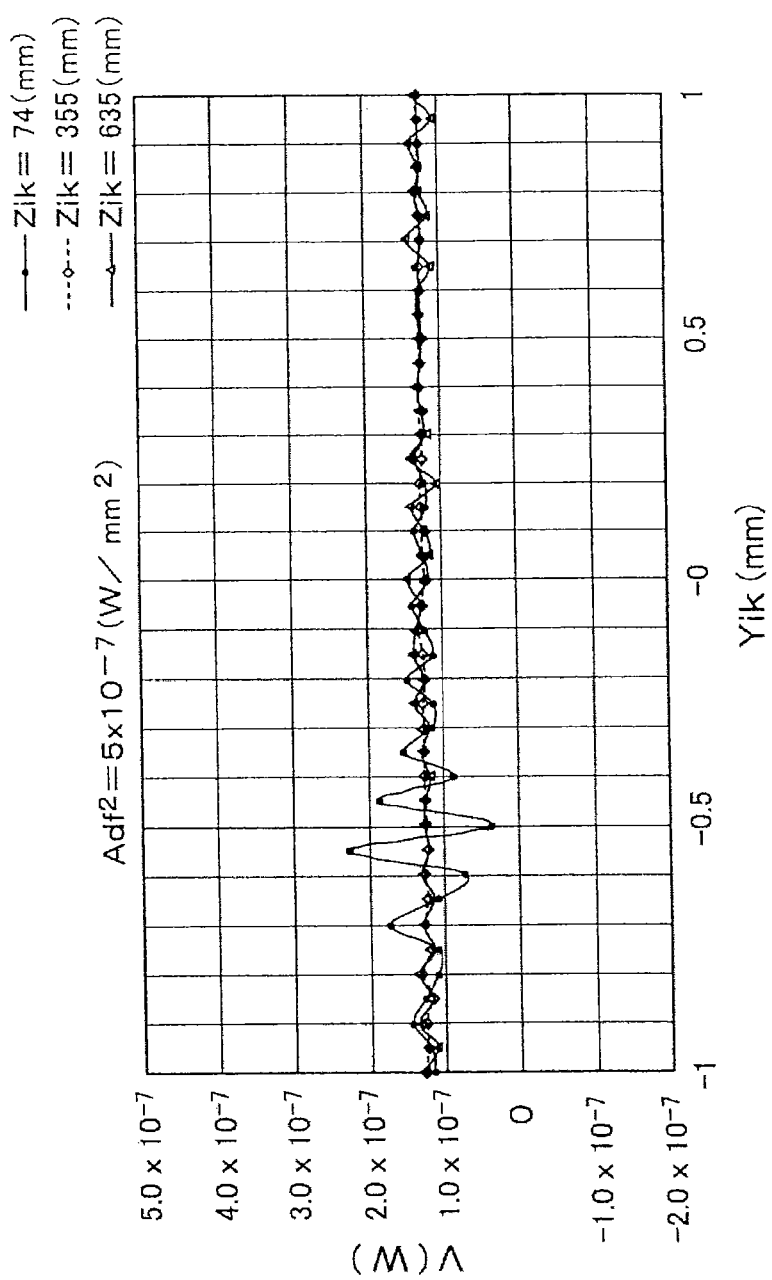
FIG. 10 is a characteristic diagram where an amount of light V entering a photodetector (PD) is obtained while setting $Adf^2=5\times10^{-7}$ W/mm$^2$.
Figure 11:
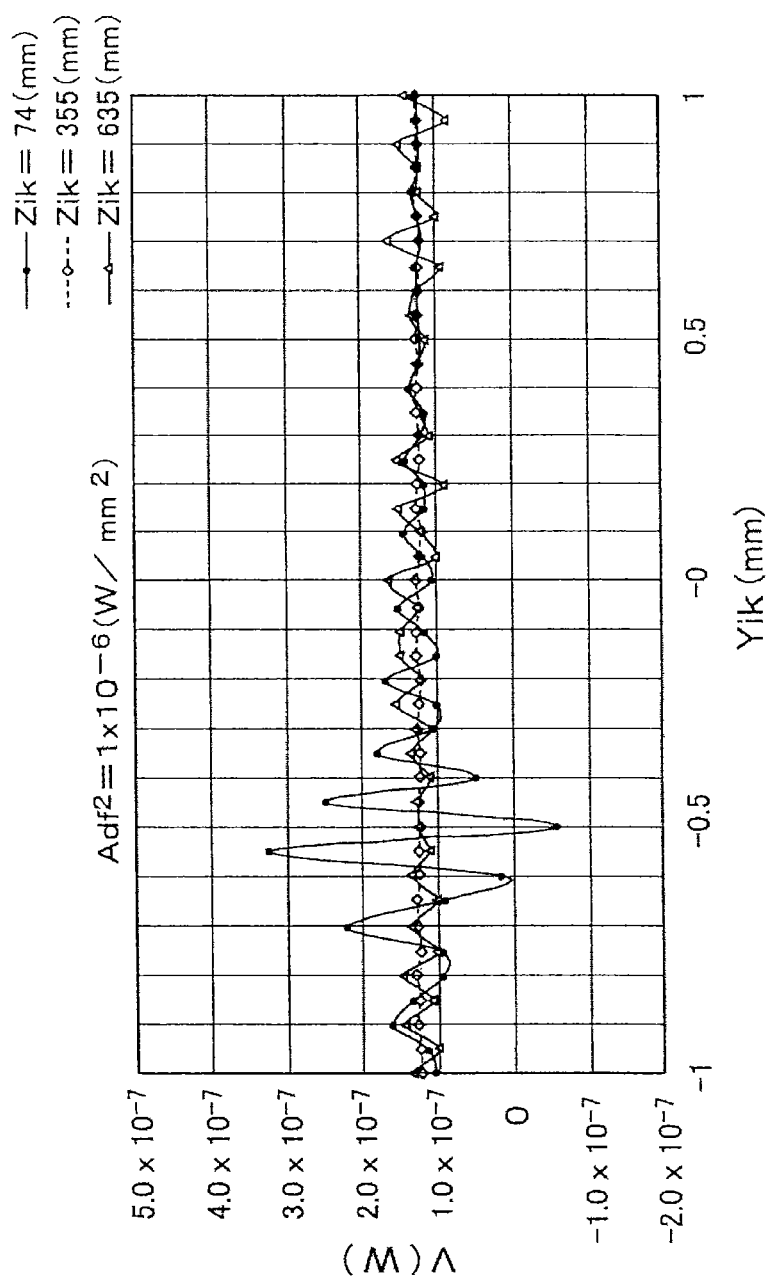
FIG. 11 is a characteristic diagram where the amount of light V entering the PD is obtained while setting $Adf^2=1\times10^{-6}$ W/mm$^2$.
Figure 12:
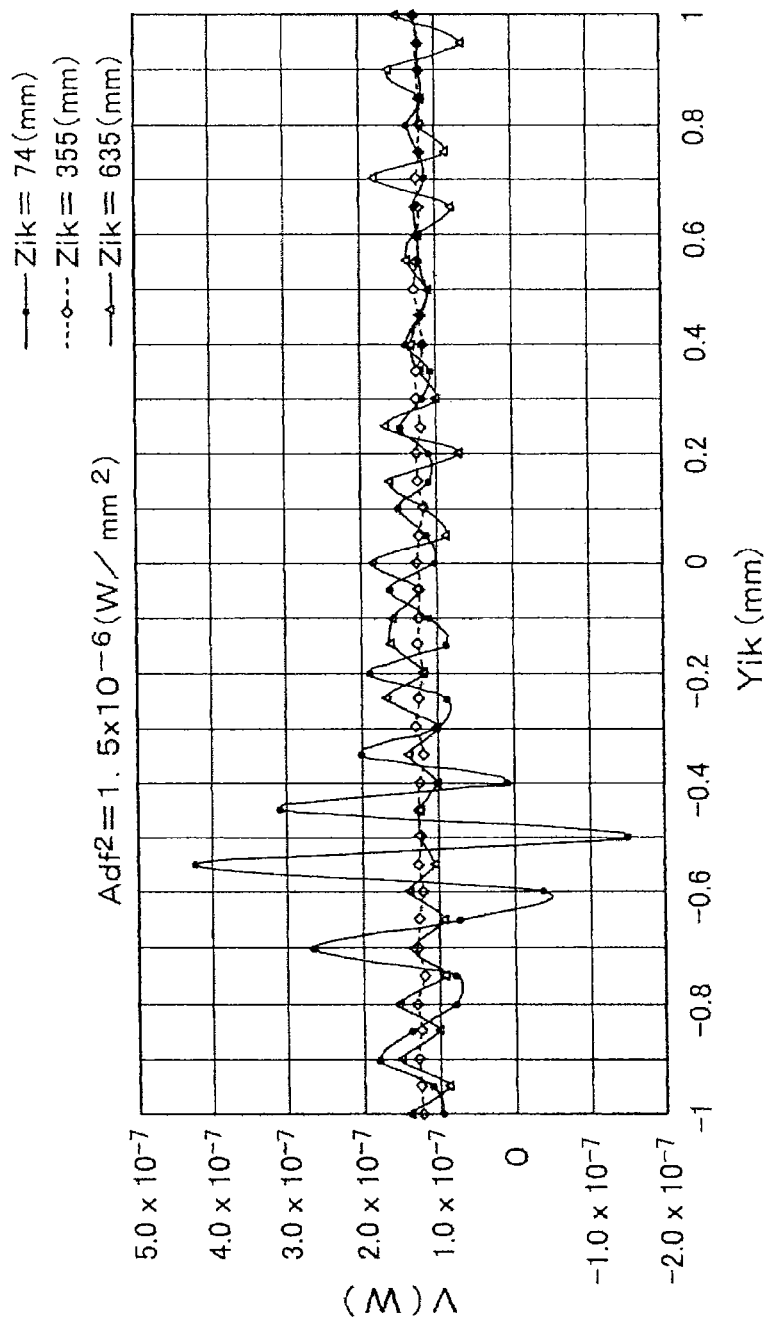
FIG. 12 is a characteristic diagram where the amount of light V entering the PD is obtained while setting $Adf^2=1.5\times 10^{-6}$ W/mm$^2$.

FIGS. 10-12 show the calculation results of the amounts of the light V entering the PD 8 for three different values of $Adf^2$ (amplitude of the diffracted light beam 11) that are obtained by using the formula (12) while varying $Y_{ik}$ in the range from −1 mm to +1 mm.

FIG. 10 shows the calculation result corresponding to the case where $Adf^2$ (amplitude of the diffracted light beam 11)=5×10$^{-7}$ W/mm$^2$, FIG. 11 shows the calculation result corresponding to the case where $Adf^2$=1×10$^{-6}$ W/mm$^2$, and FIG. 12 shows the calculation result corresponding to the case where $Adf^2$=1.5×10$^{-6}$ W/mm$^2$. In FIGS. 10-12, the horizontal axis indicates the value of $Y_{ik}$ (the Y-directional distance between the arrangement line 17 of the nozzles 6 and the optical axis 9 of the laser beam 2: mm), and the vertical axis indicates the value of V (the amount of the light entering the PD 8).

In this example, Adf and Asc are assumed to be homogeneous within the effective detection range of the PD 8. As the diffracted light beam 12 becomes stronger relative to the scattered light beam 11, the second term dominates relative to the first term in the formula (9), and thereby the variation of V with respect to the variation of $Y_{ik}$ becomes large.

In the first embodiment, for the case of FIG. 10 where $Adf^2$=5×10$^{-7}$ W/mm$^2$, the inequality V>0 is satisfied when $Y_{ik}$ is in the range from −1 mm to +1 mm. Therefore, the droplet discharge detection is possible. For the case of FIG. 11 where $Adf^2$=1×10$^{-6}$ W/mm$^2$, V becomes less than zero in the vicinity of $Y_{ik}$=−0.5 mm when $Z_{ik}$=74 mm. Therefore, the range exists where the droplet discharge detection is not possible. For the case of FIG. 12 where $Adf^2$=1.5×10$^{-6}$ W/mm$^2$, V becomes less than zero in the vicinity of $Y_{ik}$=−0.5 mm and in the vicinity of $Y_{ik}$=−0.6 mm. Therefore, the range is increased where the droplet discharge detection is not possible.

When $Z_{ik}$=74 mm, the variation of V becomes large in the vicinity of $Y_{ik}$=−0.5 mm. In this case, the center of the aperture 4, the droplet 7 and the PD 8 are substantially arranged on a straight line, and a center of curvature of the wavefront of the scattered light beam 11 and a center of curvature of the wavefront of the diffracted light beam 12 become very close to each other. When the center of curvature of the wavefront of the scattered light beam 11 and the center of curvature of the wavefront of the diffracted light beam 12 are close, the two wavefronts become similar to each other. Therefore, one of constructive interference and destructive interference dominates depending on a slight variation in the optical path difference in the effective detection range of the PD 8.

In general, the alignment error of the nozzles and the curved discharging are regulated to be less than or equal to the density of print dots. For example, the alignment error of the nozzles and the curved discharging are regulated to be less than or equal to 42 μm for 600 dpi. A positional error of the center position of the aperture 4 is due to a processing error or an installation error, for example. In general, the positional error of the center position of the aperture 4 is regulated to be within a range from −0.1 mm to +0.1 mm. An arrangement that enables the detection of discharging of the droplet may be adopted while considering the above-described errors. According to the first embodiment, discharging of the droplet can be detected if $Adf^2$<1.5×10$^{-6}$ W/mm$^2$ and $Y_{ik}$ is within a range from −0.3 mm to +0.3 mm.

Second Embodiment

Figure 13:
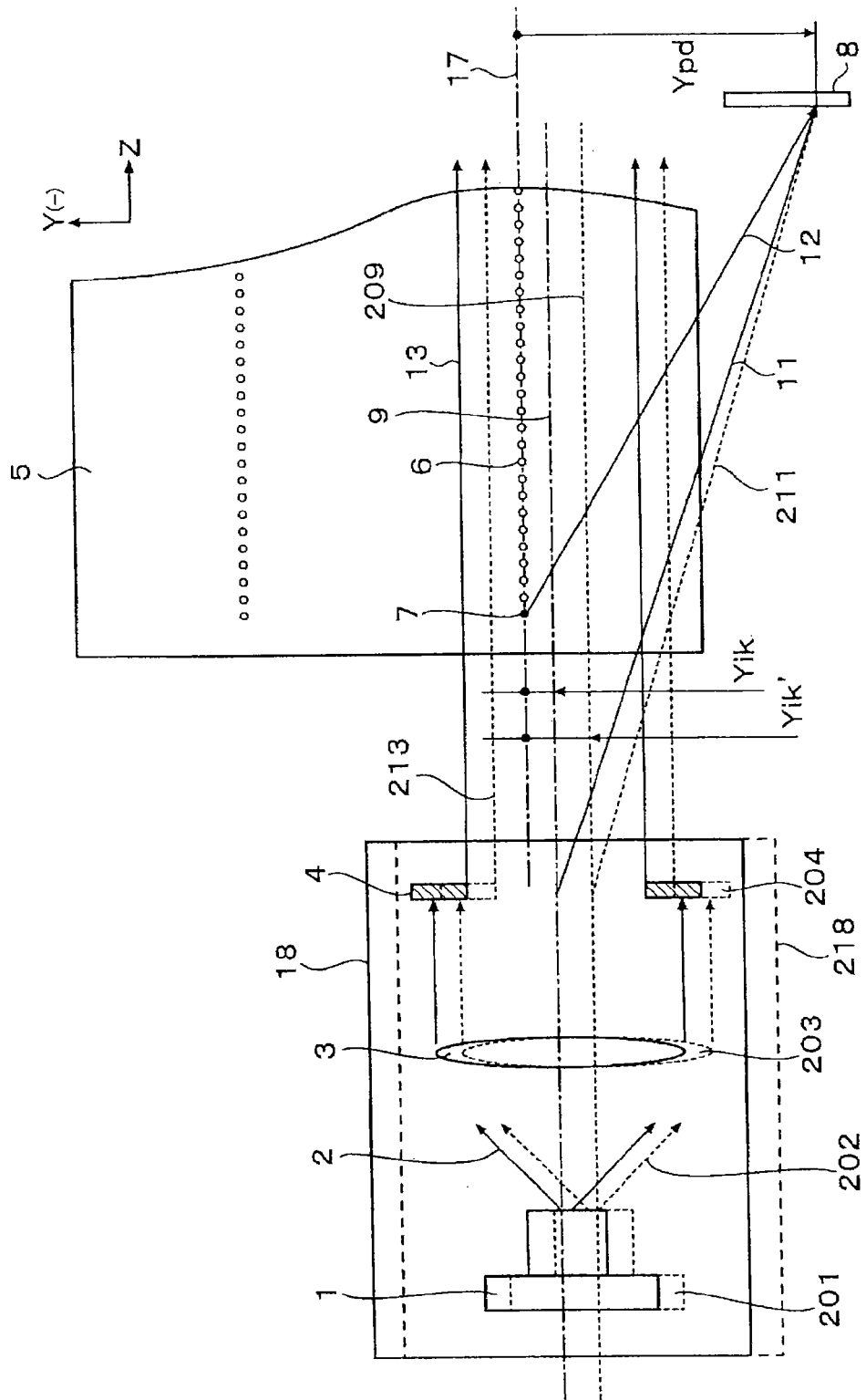
FIG. 13 is a schematic diagram illustrating the droplet discharge detection device according to a second embodiment, where the droplet discharge detection device is viewed from a top surface.

FIG. 13 is a schematic diagram of the droplet discharge detection device according to a second embodiment, where the droplet discharge detection device is viewed from a top surface. As shown in FIG. 13, the LD 1, the collimator lens 3, and the aperture 4 are integrated to form a light source unit 18. The optical axis 9 of the laser beam 2 is shifted from the line 17, along which the nozzles 6 are arranged, by the amount of $Y_{ik}$ in the Y direction. The light source unit 18 can be moved with respect to the head 5 in the Y direction. The arrangement of the light source unit 18 after moving is indicated by a dotted line.

In FIG. 13, the reference numeral 218 indicates the light source unit 18 which has been shifted in the Y direction, the reference numeral 201 indicates the LD 1 which has been shifted in the Y direction, the reference numeral 202 indicates the laser beam emitted from the LD 201, which has been shifted in the Y direction, the reference numeral 203 indicates the collimator lens 3 which has been shifted in the Y direction, the reference numeral 204 indicates the aperture 4 which has been shifted in the Y direction, the reference numeral 209 indicates the optical axis 9 of the laser beam 2 which has been shifted in the Y direction, and the reference numeral 211 indicates the diffracted light beam emitted from the light source unit 218, which has been shifted in the Y direction. The optical axis 209 is shifted by $Y_{ik}'$ in the Y direction with respect to the line 17, along which the nozzles 6 are arranged.

In the first and second embodiments, the aperture is used as an opening of the light transmitter. However, the embodiments are not limited to this configuration. For example, a configuration may be adopted such that an opening is integrated with a holder unit of the collimator lens.

In the embodiments, the "image forming device" of the liquid discharge recording type means a device which forms an image by adhering ink onto various media, such as a paper, a thread, a fiber, a fabric, a metal, a plastic, a glass, a timber, and a ceramic. Further, "forming an image" means not only to add an image having a meaning such as a character or a graphic to a medium, but also to add an image having no meaning such as a pattern to a medium (simply adhering droplets to the medium).

Further, "ink" means not only the usual ink. It is also used as a generic term of a liquid with which an image can be formed, such as a recording liquid, a fixing liquid, a resin liquid, and other various liquids. Further, "a medium to be recorded on" is not limited to the above-described sheet of paper, but it includes anything to which ink droplets may be adhered such as an OHP sheet, a cloth, a metal thin plate, and a plastic film. Namely, "a medium to be recorded on" is used as a generic term of the things that are referred to as a recording medium, a recording paper, or a data sheet, for example.

For the droplet discharge detection device according to the embodiments, within the effective range of the light receiver having a predetermined area, the interference term between the diffracted light beam emitted from the opening portion of the light emitter and the scattered light beam becomes smaller than the intensity of the scattered light beam from the droplet. Therefore, it is possible to detect the presence or absence of the discharging of the droplet.

Further, for the droplet discharge detection device according to the embodiments, the interference term between the diffracted light beam and the scattered light beam may be made smaller by the configuration in which the light emitter is movable in the Y direction with respect to the position of the nozzle. Therefore, it is possible to detect the presence or absence of the discharging of the droplet.

Further, since the image forming apparatus according to the embodiments includes the above-described droplet discharge detection device, it is possible to detect a discharging failure. Therefore, it is possible to achieve fine image quality.

The droplet discharge detection device and the image forming apparatus including the droplet discharge detection device have been explained based on the above-described embodiments. However, the present invention is not limited to the above-described embodiments, and various modifications and improvements may be made within the scope of the present invention.

The present application is based on Japanese Priority Application No. 2011-209489 filed on Sep. 26, 2011, the entire contents of which are hereby incorporated herein by reference.

What is claimed is:

1. A droplet discharge detection device comprising:
   a head array unit in which plural nozzles are arranged in a line;
   a light emitter configured to emit a light beam in a direction in which the nozzles are arranged, wherein the light emitter is disposed at a first end portion of the head array unit and the light emitter has an aperture for limiting a diameter of a light beam; and
   a light receiver configured to receive a scattered light beam of the light beam generated by a droplet, wherein the light receiver is disposed at a second end portion of the head array unit, the second end portion being opposite to the light emitter of the head array unit,
   wherein, when a first direction in which the droplet is discharged from the nozzles is set to be an X direction, and when a second direction that is perpendicular to the X direction and that is perpendicular to the direction in which the nozzles are arranged is set to be a Y direction, a formula below is satisfied, $\int_{X_1}^{X_2}\int_{Y_1}^{Y_2}(A_{sc}^2+2A_{df}\cdot A_{sc}\cdot\cos[2\pi(L_{df}-L_{sc})/\lambda])dX_{PD}\cdot dY_{PD}>0$, wherein, in the formula, the $Y_{PD}$ is a Y-coordinate of a position in the Y direction on a light receiving surface of the light receiver, the $[Y_1, Y_2]$ is an effective detection range in the Y direction on the light receiving surface of the light receiver, the $X_{PD}$ is an X-coordinate of the position in the X direction on the light receiving surface of the light receiver, the $[X_1, X_2]$ is an effective detection range in the X direction on the light receiving surface of the light receiver, the $L_{df}$ is a first optical path length of a diffracted light beam from a center of the aperture of the light emitter to the light receiving surface of the light receiver, the $A_{df}$ is a first amplitude of the diffracted light beam, the $A_{sc}$ is a second amplitude of the scattered light beam, the $L_{sc}$ is a second optical path length of the scattered light beam from the center of the aperture of the light emitter to the light receiving surface of the light receiver, and the $\lambda$ is the wavelength of the light beam.

2. The droplet discharge detection device according to claim 1,
   wherein the light receiver is disposed at a position shifted in the Y direction so as to prevent the light beam from entering, wherein the diameter of the light beam has been limited by the aperture.

3. The droplet discharge detection device according to claim 2,
   wherein the light emitter is configured to be moved in the Y direction with respect to a nozzle position at which the nozzles are arranged.

4. The droplet discharge detection device according to claim 2,
   wherein a distance $Y_{tk}$ between the line, the nozzles being arranged in the line, and an optical axis of the light beam is within a range from −0.3 mm to +0.3 mm, and
   wherein a squared value of the $A_{df}$ is less than $1.5\times10^{-6}$ W/mm$^2$.

5. An image forming apparatus comprising:
   a droplet discharge detection device,
   wherein the droplet discharge detection device includes
   a head array unit in which plural nozzles are arranged in a line;
   a light emitter configured to emit a light beam in a direction in which the nozzles are arranged, wherein the light emitter is disposed at a first end portion of the head array unit and the light emitter has an aperture for limiting a diameter of a light beam; and
   a light receiver configured to receive a scattered light beam of the light beam generated by a droplet, wherein the light receiver is disposed at a second end portion of the head array unit, the second end portion being opposite to the light emitter of the head array unit,
   wherein, when a first direction in which the droplet is discharged from the nozzles is set to be an X direction, and when a second direction that is perpendicular to the X direction and that is perpendicular to the direction in which the nozzles are arranged is set to be a Y direction, a formula below is satisfied, $$\int_{X_1}^{X_2}\int_{Y_1}^{Y_2}(Asc^2+2Adf\cdot Asc\cdot\cos[2\pi(L_{df}-L_{sc})/\lambda])dX_{PD}\cdot dY_{PD} > 0,$$

wherein, in the formula, the $Y_{PD}$ is a Y-coordinate of a position in the Y direction on a light receiving surface of the light receiver, the $[Y_1, Y_2]$ is an effective detection range in the Y direction on the light receiving surface of the light receiver, the $X_{PD}$ is an X-coordinate of the position in the X direction on the light receiving surface of the light receiver, the $[X_1, X_2]$ is an effective detection range in the X direction on the light receiving surface of the light receiver, the $L_{df}$ is a first optical path length of a diffracted light beam from a center of the aperture of the light emitter to the light receiving surface of the light receiver, the $A_{df}$ is a first amplitude of the diffracted light beam, the $A_{sc}$ is a second amplitude of the scattered light beam, the $L_{sc}$ is a second optical path length of the scattered light beam from the center of the aperture of the light emitter to the light receiving surface of the light receiver, and the $\lambda$ is the wavelength of the light beam.

* * * * *